United States Patent [19]
Ferrer et al.

[11] Patent Number: 5,919,688
[45] Date of Patent: Jul. 6, 1999

[54] ENZYME WITH B-1, 3-GLUCANASE ACTIVITY

[75] Inventors: Pau Ferrer, Esplugues De Llobregat, Spain; Ivan Diers, Bagsværd, Denmark; Lisbeth Hedegaard, Skodsborg, Denmark; Torben Halkier, Frederiksberg, Denmark; Juan A. Asenjo, Santiago, Chile; Demitris Savva, Reading, United Kingdom

[73] Assignee: Novo Nordisk A/S, Bagsvaerd, Denmark

[21] Appl. No.: 08/824,707

[22] Filed: Apr. 14, 1997

Related U.S. Application Data

[63] Continuation of application No. PCT/DK95/00414, Oct. 16, 1995.

[30] Foreign Application Priority Data

Oct. 14, 1994 [DK] Denmark ................................ 1192/94

[51] Int. Cl.⁶ .............................. C12N 9/24; C12N 15/56; C12N 15/75; C12N 15/80
[52] U.S. Cl. .................... 435/200; 435/69.1; 435/252.3; 435/252.31; 435/320.1; 536/23.2; 935/14; 935/29; 935/72; 935/74
[58] Field of Search .................................. 435/200, 69.1, 435/252.3, 252.33, 254.11, 320.1, 252.31; 536/23.2

[56] References Cited

U.S. PATENT DOCUMENTS

| 4,576,914 | 3/1986 | Yoshida et al. ............................ 435/42 |
| 5,290,916 | 3/1994 | Matsushrio .............................. 530/350 |
| 5,306,639 | 4/1994 | Matsushiro ............................ 435/320.1 |
| 5,470,725 | 11/1995 | Borriss et al. ............................. 435/93 |
| 5,631,007 | 5/1997 | Ryals et al. ............................ 424/94.61 |

FOREIGN PATENT DOCUMENTS

| 0 440 304 A1 | 8/1991 | European Pat. Off. . |
| 3-53883 | 3/1991 | Japan . |
| WO 87/01388 | 3/1987 | WIPO . |
| WO 92/03557 | 3/1992 | WIPO . |
| WO 92/16632 | 10/1992 | WIPO . |
| WO 96/12103 | 4/1996 | WIPO . |

OTHER PUBLICATIONS

Yahata, N., et al., Gene, vol. 86, "Structure of the gene encoding beta–1,3–glucanase A1 of Bacillus circulans WL–12", pp. 113–117, 1991.

Ferrer, P., et al., Annals of the New York Academy of Sciences, vol. 782, "Molecular cloning of a lytic beta–1, 3–glucanase gene from Oerskovia xanthineolytica LLG109", pp. 555–565, 1996.

Ferrer, P., et al., Journal of Bacteriology, vol. 178, "Nucleotide Sequence of a beta–1,3–glucanse isoenzyme IIA gene of Oerskovia xanthineolytica LLG109 and initial characterization of the recombinant enzyme expressed in Bacillus subtilis", pp. 4751–4754, 1996.

Janet H. Scott et al., "Lyticase: Endoglucanase And Protease Activities That Act Together In Yeast Cell Lysis", Journal of Bacteriology, May 1980, pp. 414–423, vol. 14L.

Remi Spilliaert et al., (1994) Cloning And Sequencing Of A Rhodothermus Marinus Gene, bg1A, Coding For A Thermostable β–Glucanase And Its Expression In *Escherichia Coli*, European Journal of Biochemistry vol. 224 pp. 923–930.

(List continued on next page.)

*Primary Examiner*—Robert A. Wax
*Assistant Examiner*—William W. Moore
*Attorney, Agent, or Firm*—Steveti Zelson, Esq.; Valeta Gregg, Esq.

[57] ABSTRACT

A DNA construct exhibiting β-1,3-glucanase activity, including an expression vectors, cells harbouring the DNA construct or expression vector, a method of producing the enzyme, as well as the enzyme and preparations containing the enzyme.

18 Claims, 5 Drawing Sheets

OTHER PUBLICATIONS

Thomas W. Jeffries et al., "Action Patterns Of (1–3) β–DGlucanases From Oerskovia Xanthineolytica On Laminaran, Lichenan, And Yeast Glucan", Carbohydrate Research, 95 (1981) pp. 87–100.

B.A. Andrews et al., "Continuous–Culture Studies of Synthesis And Regulation of Extracellular β(1–3) Glucanase and Protease Enzymes From Oerskovia Xanthineolytica", Biotechnology and Bioengineering, vol. 30, pp. 628–637 (1987).

J.W. Mann et al., "Production And Ecological Significance Of Yeast Cell Wall–Degrading Enzymes From Oerskovia", Applied And Environmental Microbiology, Oct. 1978, vol. 36, No. 4, pp. 594–605.

Shi–Hsiang Shen et al., "Primary Sequence Of The Glucanase Gene From Oerskovia Xanthineolytica", The Journal of Biological Chemistry, vol. 266, No. 2, Issue of Jan. 15, pp. 1058–1063, 1991.

A.M. Ventom et al., "Characterizaton Of Yeast Lytic Enzymes From Oerskovia Xanthineolytica" Enzyme Microb. Technol., 1991, vol. 13, Jan., pp. 71–75.

Hitoshi Shimoi et al., "Characterization of Rarobacter Faecitabidus Protease I, A Yeast–Lytic Serine Protease Having Mannose–Binding Activity", J. Biochem. 110, pp. 608–613, 1991.

Mami Yamamoto et al., "Structure Of The 87–kDa β–1, 3–Glucanase Gene of Bacillus Circulans IAM1165 And Properties Of The Enzyme Accumulated In The Periplasm Of Escherichia Coli Carrying The Gene", Biosci Biotech., 57(9). pp. 1518–1525, 1993.

Takeshi Wantanabe et al., "Three N–Terminal Domains Of β–1,3–Glucanase A1 Are Involved In Binding To Insoluble β–1, 3–Glucan", Journal of Bacteriology, Jan. 1992, pp. 186–190.

Kenji Doi et al., "Cloning and Expression In Escherichia Coli Of The Gene For An Arthrobacter β–(1–3)–Glucanase", Journal of Bacteriology, Dec. 1986, pp. 1272–1276.

```
BamHI
ggatccggtgatgcgcgaaaccttcgtcatgagggttcggtgcgcttgagacgccccgc
gctgtcctaccgctggtgaggacggcgcacaccgtccggtgcatcattcgggacgtcggg
cccaggaggtggtcggcatcaaatcacggcatcgttcggatgacactcttcaccgttgag
ccggggcaacaacctgtggtcctcgttcggaggagctcgtcgcagccctcgtgtcagagg
tgccgcttcgacgccggcccaggagatacgggtcgcgcagaccctcaccacgtgcgaca
                                                          360
ccgcggacccacaccgacgatgaaggctctgccggcagatctcggagagatgatgagcct
                                                M  S  L  -
                                                       420
cccgcatgagccgtcctcgccttcaaggcgaaccctcacgttgatcctggccgctgctgc
 P  H  E  P  S  S  P  S  R  R  T  L  T  L  I  L  A  A  A  A -
                                                       480
tggtctcgcactggtggccgcctggatcgtcatcgccaccaggtcgtcgccaccgacgag
 G  L  A  L  V  A  A  W  I  V  T  A  T  R  S  S  P  P  T  S -
                                                       540
tcctcccaccacagaaggcggccaggtcacgacccagcccccaacgacccacgccgt
 P  P  T  T  E  G  G  Q  V  T  T  P  A  P  N  D  P  T  A  V -
                                                       600
caccccgagagcctcgcctggtccgacgagttcgacggcgccgcggggtcggcgccgaa
 T  P  E  S  L  A  W  S  D  E  F  D  G  A  A  G  S  A  P  N -
 A  P  G  D  L  L  W  S  D  E  F                      660
ccccgacgtgtggaaccacgagaccggcgccggcggttggggcaacgccgagctccagaa
 P  D  V  W  N  H  E  T  G  A  G  W  G  N  A  E  L  Q  N -
                                                       720
ctacacgacgtcgcgggtgaactcggcgctcgacggtcagggcaacctggtcatcaccgc
 Y  T  T  S  R  V  N  S  A  L  D  G  Q  G  N  L  V  I  T  A -
                                                       780
gctccaggagagcgacgggtcgtacacgtccgcacgcttgaccacgcagggcaacgtcca
 L  Q  E  S  D  G  S  Y  T  S  A  R  L  T  T  Q  G  N  V  Q -
                                                     Y  Q
gccgcagttcggtcgaatagaggcgcgcatccagatcccgcgtggccagggcatctggtc
 P  Q  F  G  R  I  E  A  R  I  Q  I  P  R  G  Q  G  I  W  S -
 P  Q  Y  G  R  I  E  A  R  R  Q  I  P  R  G        900
cgcgttctggatggtcggagcgaacctgcccgacacccctggcctacctccggtgagat
 A  F  W  M  V  G  A  N  L  P  D  T  P  W  P  T  S  C  E  I -
                                                       960
cgacatcatggagaacgtgggcaatgcgccccacgaggtccacggcacggtccacgggcc
 D  I  M  E  N  V  G  N  A  P  H  E  V  H  C  T  V  H  G  P -
                                                       1020
tgggtactccggggacaacggcatcatgggcacctaccagcatccgcaagggtggtcgtt
 G  Y  S  G  D  N  G  I  M  G  T  Y  Q  H  P  Q  G  W  S  F -
                                                       1080
cgccgacgacttccacaccttcggcatcgattggacgccgggtgagatcacgtggctcgt
 A  D  D  F  H  T  F  G  I  D  W  T  P  G  E  I  T  W  L  V -
                                                     F  V
tgacgggcaggagtatcaccgcgtgacgaccgcggatgtcggtgccaaccagtgggtgtt
 D  G  Q  E  Y  H  R  V  T  T  A  D  V  G  A  N  Q  W  V  F -
 D  G  Q  Q  F  X  R  V                              1200
cgaccagccgttcttcctcatcctcaacgtcgccatcggcggccagtggcccggcaaccc
 D  Q  P  F  F  L  I  L  N  V  A  I  G  G  Q  W  P  G  N  P -
                V  A  V  G  G  Q  W  P  C  Y  P
cgacgcaacgaccccgtttccgcagcagatgaaggtcgactacgtgcgggtctacgacaa
 D  A  T  T  P  F  P  Q  Q  M  K  V  D  Y  V  R  V  Y  D  N -
 D                             D  Y  V  R  V  Y  D
cgcgacgcagtagccaccctcgcgcgggcgccgccggttcgatcgggaacgggtcgagac
 A  T  Q  *                                          1320
gctggtgggtgaacgaccagcgtcgacctggggcaacctgaccgttgctggtgcagctcg
gtcatcctgtgactccggggtctacggcggatgcgcatcgtcgctgccgccggacgggc
ggtaggtgcgtcaggtacc
        KpnI            FIG. 3
```

ENZYME WITH B-1, 3-GLUCANASE ACTIVITY

CROSS-REFERENCE TO RELATED APPLICATIONS

This application is a continuation of PCT/DJK95/00414 filed 16 Oct. 1995, which claims priority under 35 U.S.C. 119 of Danish application 1192/94 filed 14 Oct. 1994, the contents of which applications are fully incorporated herein by reference.

FIELD OF THE INVENTION

The present invention relates to a novel enzyme exhibiting β-1,3-glucanase activity. More specifically a DNA construct encoding the novel enzyme, an expression vector comprising said DNA construct, a cell comprising said DNA construct or said recombinant expression vector, a method of producing said novel enzyme, an enzyme preparation comprising said novel enzyme, and use of the enzyme for degradation or modification of β-glucan containing material.

BACKGROUND OF THE INVENTION

A large diverse group of nonmotile, heterotrophic, eukaryotic organisms are collectively referred to as fungi. Most fungi are saprophytes, i.e. securing their food from dead organic material. Because of their heterotrophic properties, i.e. using organic material as carbon source, many fungi produce metabolites of industrial interest. Certain species are further useful as sources for food, whereas others are responsible for spoiling almost any organic material in which they come in contact.

Fungal cells range in size from microscopic unicellular organisms to macroscopic as e.g. mushrooms. True fungi are in general terrestrial and includes Zygomycetes, such as Rhizopus, Basidiomycetes such as *Puccinia graminis*, Ascomycetes, such as Neurospora and Saccharomyces and Deuteromycetes, such as Penicillium and Aspergillus.

Fungal cells

Fungal microorganisms include multicellular as well as unicellular organisms and are in general considered to consist of yeasts and molds. Unicellular fungi are primarily yeasts, while the term mold is used for fungi that are predominantly mycelial.

Fungal cells have a quite complex structure, constituting of a cytoplasm, comprising nucleus, mitochondria, microbodies etc. encapsulated by a cytoplasmic membrane. Chemically and structurally the cytoplasmic membrane consist of a bilayer of phospholipids with different proteins inserted into it.

The cytoplasmic membrane is surrounded by the rigid cell wall.

Structure of fungal cell walls

The cell walls of most true fungal microorganisms contain a network of glucan, which gives the cell wall strength. Further major fungal cell walls constituents are mannoprotein and chitin.

Glucan and chitin is far more resistant to microbial degradation than cellulose, which is the major constituent of the cell wall of many fungi-like organisms, such as Oomycetes.

Glucan is predominantly β-1,3-linked with some branching via 1,6-linkage (Manners et al., Biotechnol. Bioeng, 38, p. 977, 1973), and is known to be degradable by certain β-1,3-glucanase systems.

β-1,3-glucanase includes the group of endo-β-1,3-glucanases also called laminarinases (E.C. 3.2.1.39 and B.C. 3.2.1.6, Enzyme Nomenclature, Academic Press, Inc, 1992).

Pegg et al., Physiol. Plant Pathol., 21, p. 389–409, 1982, showed that a purified endo-β-1,3-glucanase from tomato in combination with an exo-β-1,3-glucanase of fungal origin were capable of hydrolysing isolated cell wall of the fungus *Verticillium alboatrum*.

Further, Keen et al., Plant Physiol., 71, p. 460–465 showed that a purified β-1,3-glucanase from soy bean was capable of degrading isolated cell walls of fungi.

Large scale degradation of the fungal cell wall

The unit operation of cell disruption appears as an essential first step for intracellular products separation and downstream processing of valuable intracellular products.

Large scale cell disruption is in general carried out by rather vigorous treatment involving the use of strong chemicals and/or mechanical means. This leaves the target protein with a very complex mixture of contaminants.

In this context extensive industrial implementation of alternative approaches to conventional microbial cell disruption techniques are becoming of increasing relevance (Asenjo et al., Bio/technol, 11, p. 214, 1993; De la Fuente et al., Appl. Microbiol. Biotechnol, 38, p. 763, 1993).

Selective Cell Permeabilization (SCP) and Selective Protein Recovery (SPR) as a mean to increase bio-process productivity, economy and product quality by simplifying the downstream processing of intracellular products have proved to be very attractive in terms of their delicacy and specificity (Asenjo et al., 1993, supra; Shen et al., Gene, 84, P. 1989).

SCP and SPR involves the use of pure preparations of cell-wall-degrading β-glucanases to increase fungal cell wall porosity (with very limited cell lysis) and facilitate the release of intracellular proteins. In this way, SCP gives primary separation of the target product from some of its major contaminants. A major limitation to this approach is the relatively low level of expression of yeast lytic enzymes presently obtained in the bacteria used for the production of these enzymes (e.g. *Oerskovia xanthineolytica*, Andrews and Asenjo, Biotech. Bioeng, 30, p. 628, 1987). Today *Oerskovia xanthineolytica* are sometimes referred to as *Cellulomonas cellulans*. However, the name *Oerskovia xanthineolytica* will be used below.

A number of commercial enzyme compositions useful in the enzymatic lysis of fungal cells are available. Such products normally comprise multiple enzymatic activities, e.g. including β-1,3- and β-1,6-glucanase, protease, chitinase, mannase and other enzymes capable of degrading cell wall components.

The lytic system of *Oerskovia xanthineolytica* LLG109

The lytic enzyme system of *Oerskovia xanthineolytica* LLG109 has partially been isolated and purified and some of the glucanase and protease components have been characterised (Ventom and Asenjo, Enzyme Microb. Technol., 13, p. 71, 1991).

Although a single molecular species of lytic β-1,3-glucanase has been characterized from *O. xanthineolytica* LLG109, most Oerskovia strains seem to have multiple β-1,3-glucanase systems (Doi and Doi, J. Bacteriol., 168, p. 1272, 1986).

While all observed molecular forms of these enzymes possess hydrolytic activity towards β-1,3-glucans (β-1,3-glucanase activity), only some are found capable of readily solubilizing yeast glucan and inducing lysis of viable yeast cells.

In contrast, other types of endo-β-1,3-glucanases would solubilize yeast glucan only partially, causing only limited cell lysis (Doi and Doi, supra, 1986). However, this multitude of enzyme species produced by Oerskovia may be partially due to proteolytic processing.

The genetic relationship between these enzymes is still unclear, as the number of yeast lytic enzymes so far cloned is very limited. As a result, there is still limited knowledge about the gene structure and protein function relationship (Shen et al, J. Biol. Chem, 266, p. 1058, 1991; Shimol and Tademura, J. Biochem, 110, 608, 1991; Watanabe et al., J. Bacteriol, 174(1), p. 186, 1992; Yamamoto et al., Biosci. Biotechnol. Biochem., 57, p. 1518–1525, 1993).

Characterization of yeast lytic enzymes from *O. xanthineolytica*

A purified lytic β-1,3-glucanase showed a molecular mass of about 31 kDa, when estimated by SDS-PAGE and a pI of 5.0. The amino acid composition was also determined. The yield was optimized by the continuous culture process, but yields were still low.

The specific activity of the enzyme was 11.1 U/mg. The $K_m$ for β-1,3-glucanase activity on yeast glucan was 2.5 mg/ml for laminarin (a soluble β-1,3-glucan) 0.95 mg/ml. The pH optimum for β-1,3-glucanase was 8.0 on yeast glucan and 6.0 on laminarin substrate. The lytic β-1,3-glucanase caused only limited lytic activity on viable yeast (*Saccharomyces cerevisiae*) cells (Ventom and Asenjo, supra, 1991), but this was stimulated synergistically by the lytic protease component.

In addition, there was detected another β-1,3-glucanase component in clarified O. xanthineolyticacontinuous fermentation broth, although it was not purified to homogeneity and subsequently characterized.

Patent documents

A number of β-1,3-glucanase genes and uses thereof have been sought patented.

An example is DD 226012 (Akad. Wissenshaft DDR) which concerns a method for production of a Bacillus β-1,3-glucanase. Further, JP 61040792 A (DOE K) describes a cell wall-cytolase β-1,3-glucanase recombinant plasmid for removing the cell walls of yeast. The gene is derived from Arthrobacter and is transformed into Escherichia group bacteria.

EP 440.304 concerns plants provided with improved resistance against pathogenic fungi transformed with at least one gene encoding an intracellular chitinase, or an intra- or extracellular β-1,3-glucanase. The matching recombinant polynucleotides is also disclosed.

WO 87/01388 describes a method for preparing cell lytic enzymes, such as β-1,3-glucanases, which can be produced by Oerskovia.

WO 92/03557 discloses a recombinant DNA expression vector comprising a 2.7 kb DNA sequence, derived from *Oerskovia xanthineolytica*, encoding a β-1,3-glucanase. Said glucanase, expressed in *E. coli*, exhibits glucanase activity and no protease activity. *E. coli* has a number of deficiencies in connection with large scale industrial enzyme production. First of all the glucanase is expressed intercellular. Consequently the cells need to be opened to get access to the enzyme. This makes recovery of the enzyme cumbersome and expensive.

From WO 92/16632 a recombinant DNA sequence coding for a novel protein with β-1,3-glucanase activity is known. The gene is derived from soy.

Most presently available enzyme preparations for the use of lysing furngal cells contain protease activity, which leaves the lysed target protein with a very complex mixture of contaminants.

It is therefore desirable to provide a β-1,3-glucanase substantially free of protease activity which is capable of opening the cell walls in a gentle way. This will facilitate the recovery and purification of the target protein.

Further, it would be advantageous to express the gene encoding the target protein in a heterologous host cell capable of increasing the production yield.

SUMMARY OF THE INVENTION

The present inventors have surprisingly succeeded in solving some of the above mentioned problems by providing a novel β-1,3-glucanase.

First of all they have isolated and characterized a novel DNA sequence encoding a novel 26 kDa enzyme exhibiting β-1,3-glucanase activity. According to the invention it is possible to prepare a novel single-component β-1,3-glucanase.

Accordingly, in a first aspect the invention relates to a DNA construct comprising a DNA sequence encoding a novel enzyme exhibiting β-1,3-glucanase activity, which DNA sequence a) comprises the DNA sequence shown in SEQ ID No. 1, or b) comprises an analogue of the DNA sequence shown in SEQ ID No. 1, which i) hybridizes with the same oligonucleotide probe as the DNA sequence shown in SEQ ID No. 1, and ii) encodes a polypeptide which is homologous with the polypeptide encoded by a DNA sequence comprising the DNA sequence shown in SEQ ID No. 1, or iii) encodes a polypeptide which is immunologically reactive with an antibody raised against a purified β-1,3-glucanase encoded by the DNA sequence shown in SEQ ID No. 1 derived from Oerskovia xanthineolytica LLG109.

The *Oerskovia xanthineolytica* LLG109 strain has been deposited by the inventors according to the Budapest Treaty at the Deutshe Sammiung von Mikroorganismen und Zellkulturen GmbH., (DSM).

In the present context the expression "analogue" of the DNA sequence shown in SEQ ID No. 1 is intended to indicate any DNA sequence encoding an enzyme exhibiting β-1,3-glucanase activity which has the properties i)–iii) above. Typically, the analogous DNA sequence is isolated from another or related (e.g. the same) organism known or contemplated to produce the enzyme with β-1,3-glucanase activity on the basis of any of the DNA sequences shown in SEQ ID No. 1, e.g. using the procedures described herein, or is constructed on the basis of the DNA sequence shown in SEQ ID No. 1, e.g. by introduction of nucleotide substitutions which do not give rise to another amino acid sequence of the β-1,3-glucanase encoded by the DNA sequence, but which correspond to the codon usage of the host organism intended for production of the enzyme, or by introduction of nucleotide substitutions which do give rise to a different amino acid sequence and therefore, possibly, a different protein structure which might give rise to a β-1,3-glucanase mutant with different properties than the native enzyme. Other examples of possible modifications are insertion of one or more nucleotides into the sequence, addition of one or more nucleotides at either end of the sequence, or deletion of one or more nucleotides at either end or within the sequence. For instance, the analogous DNA sequence may be a subsequence of the DNA sequences shown in SEQ ID No. 1, for which the encoded protein exhibits β-1,3-glucanase activity.

The hybridization referred to in i) above is intended to indicate that the analogous DNA sequence hybridizes to the same probe as the DNA sequence encoding the novel 26 kDa β-1,3-glucanase enzyme under certain specified conditions which are described in detail in the Materials and Methods section hereinafter.

Normally, the analogous DNA sequence is highly homologous to the DNA sequence such as at least 60% homologous to the sequence shown above encoding a 1,3-glucanase of the invention, such as at least 70%, at least 75%, at least 80%, at least 85%, at least 90% or even at least 95% homologous to the sequence shown in SEQ ID no. 1 below.

The degree of homology referred to in ii) above is determined as the degree of identity between the two sequences indicating a derivation of the first sequence from the second. The homology may suitably be determined by means of computer programs known in the art such as GAP provided in the GCG program package (Needleman, S. B. and Wunsch, C.D., (1970), Journal of Molecular Biology, 48, 443–453). Using GAP with the following settings for DNA sequence comparison: GAP creation penalty of 5.0 and GAP extension penalty of 0.3, the coding region of the DNA sequence exhibits a degree of identity preferably of at least 60%, such as at least 75% or 90% with the enzyme encoded by a DNA construct comprising the DNA sequence SEQ ID No. 1.

The term "derived from" in connection with property iii) above is intended not only to indicate a β-1,3-glucanase produced by Oerskovia xanthineolytica LLG109, but also a β-1,3-glucanase encoded by a DNA sequence isolated from Oerskovia xanthineolytica LLG109 and produced in a host organism transformed with a vector comprising said DNA sequence.

The immunological reactivity may be determined by the method described in the Materials and Methods section below.

In a further aspect, the invention relates to the construction of an expression vector harbouring a DNA construct of the invention, a cell comprising the DNA construct or expression vector, and a method of producing a novel enzyme exhibiting β-1,3-glucanase activity, which method comprises culturing said cell under conditions permitting the production of the enzyme, and recovering the enzyme from the culture.

Still in a further aspect, the invention relates to a novel enzyme exhibiting β-1,3-glucanase activity, which enzyme
a) is encoded by a DNA construct of the invention
b) produced by the method of the invention, and/or
c) is immunologically reactive with an antibody raised against a purified β-1,3-glucanase encoded by the DNA sequence shown in SEQ ID No. 1 derived from Oerskovia xanthineolytica LLG109.

The present invention also relates to an enzyme preparation useful for the degradation or modification of β-glucan containing materials, in particular microbial cell wall material, said composition being enriched by an enzyme exhibiting β-1,3,-glucanase activity, as described above.

Finally contemplated according to the invention is the use of the novel enzyme or the enzyme preparation for preparation of fungal protoplasts or fungal extracts, especially yeast extracts.

An object of the invention is to provide a process for recovery of biological components from fungal cells, by subjecting the fungal cells in question to the novel β-1,3-glucanase or an enzyme preparation thereof.

BRIEF DESCRIPTION OF THE DRAWING

FIG. 3 shows the 1.5 kb BamHI-KpnI fragment sequence according to the invention with compared with the predicted amino acid sequence and the partially determined amino acid sequence.

DETAILED DESCRIPTION OF THE INVENTION

Figure 1:
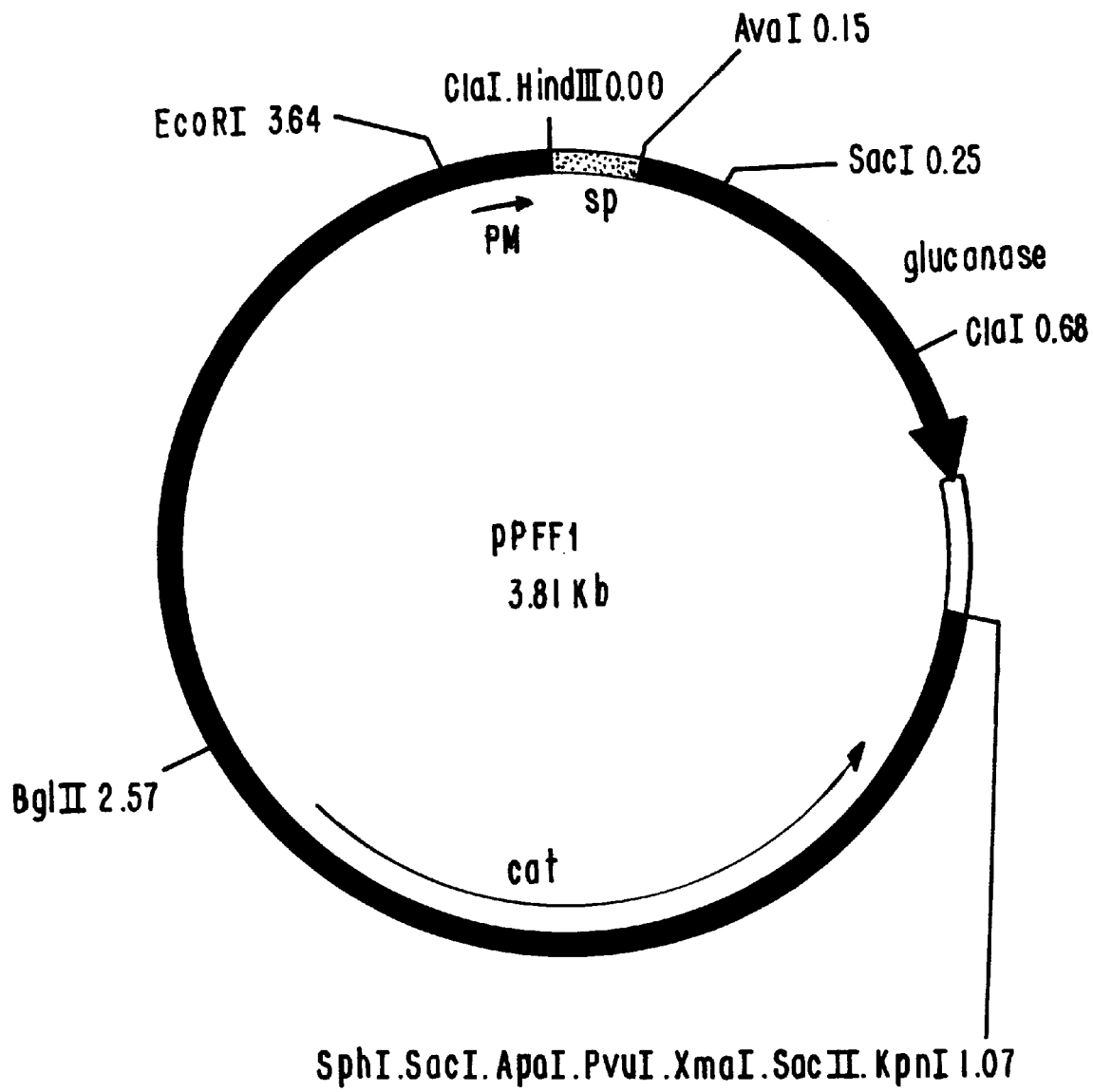
FIG. 1 shows the map of plasmid pPFF1.

The present inventors have now surprisingly succeeded in providing a novel β-1,3-glucanase substantially free of protease activity. By using the novel β-1,3-glucanase to get access to the desired intercellular component facilitates the recovery process. The novel enzyme opens up the cells in a gently way, which involves making large and porous pores in the cell walls. This will further lead to a reduced amount of contaminants.

Furthermore, the inventors have accomplished to express the gene encoding the novel β-1,3-glucanase in a suitable heterologous host cell. Specifically in a strain of Bacillus subtilis, suitable for large scale industrial production. The yield of the novel β-1,3-glucanase is increased in comparison to the parent cell from which the gene originates.

The DNA sequence of the invention encoding an enzyme exhibiting β-1,3-glucanase activity may be isolated by a general method involving
  cloning, in suitable vectors, a DNA construct from Oerskovia xanthineolytica LLG109,
  transforming suitable host cells with said vectors,
  culturing the host cells under suitable conditions to express any enzyme of interest,
  screening for positive clones by determining any β-1,3-glucanase activity of the enzyme produced by such clones,
  selection of clones, and
  isolating the enzyme encoding DNA from such clones.

The general method is further disclosed in WO 93/11249 which is hereby incorporated by reference. A more detailed description of the method is given below.

The DNA sequence coding for the enzyme may for instance be isolated from Oerskovia xanthineolytica strain LLG109 (Lechevalier, Int. J. Sys. Bacteriol., 22(4), p. 260, 1972), and selecting for clones expressing the appropriate enzyme activity (i.e. β-1,3-glucanase activity as defined by the ability of the enzyme to hydrolyse β-1,3-glucan bonds of a suitable substrate such as laminarin or AZCL-curdlan, cf. the Materials and Methods section hereinafter).

The Oerskovia xanthineolytica LLG109 strain has been deposited by the inventors according to the Budapest Treaty on the International Recognition of the Deposit of Microorganisms for the Purposes of Patent Procedure at the Deutshe Sammlung von Mikroorganismen und Zellkulturen GmbH., (DSM).

Deposit date: 13.10.95
Depositor's ref.: NN049107 (Oerskovia xanthineolytica LLG109)
DSM designation: Oerskovia xanthineolytica (or Cellulomonas cellulans) DSM No. 10297.

Being an International Depository Authority under the Budapest Treaty, Deutshe Sammlung von Mikroorganismen und Zellkulturen GmbH., affords permanence of the deposit in accordance with the rules and regulations of said treaty, vide in particular Rule 9. Access to the deposit will be available during the pendency of this patent application to one determined by the Commissioner of the United States Patent and Trademark Office to be entitled thereto under 37 C.F.R. Par. 1.14 and 35 U.S.C. Par. 122. Also, the above mentioned deposits fulfil the requirements of European patent applications relating to micro-organisms according to Rule 28 EPC.

The above mentioned deposit represent substantially pure cultures of the isolated bacteria. The deposit is available as required by foreign patent laws in countries wherein counterparts of the subject application, or its progeny are filed. However, it should be understood that the availability of the deposited strains does not constitute a license to practice the subject invention in derogation of patent rights granted by governmental action.

The appropriate DNA sequence may then be isolated from the clone by standard procedures, e.g. as described in Materials and Methods section.

According to the invention the DNA construct comprises a DNA sequence, which a) comprises the DNA sequence shown in SEQ ID No. 1, or
b) comprises an analogue of the DNA sequence shown in SEQ ID No. 1, which
   i) hybridizes with the same oligonucleotide probe as the DNA sequence shown in SEQ ID No. 1, and
   ii) encodes a polypeptide which is homologous with the polypeptide encoded by a DNA sequence comprising the DNA sequence shown in SEQ ID No. 1, or
   iii) encodes a polypeptide which is immunologically reactive with an antibody raised against a purified β-1,3-glucanase encoded by the DNA sequence shown in SEQ ID No. 1 derived from *Oerskovia xanthineolytica* LLG109.

In an embodiment of the invention the DNA construct comprises the sequence shown in SEQ ID No. 1 or SEQ ID No. 3.

The polypeptide encoded by said DNA sequences shown in SEQ ID No. 1 and SEQ ID No. 3 are shown in SEQ ID No. 2 and SEQ ID No. 3.

A preferred method of amplifying specific DNA sequences are by the use of polymerase chain reaction (PCR) using degenerate oligonucleotide probes synthesized. For instance, the PCR may be carried out using the techniques described in U.S. Pat. No. 4,683,202 or by R. K. Saiki et al. (1988), Science, 239, 487–491

It is expected that a DNA sequence coding for a homologous enzyme, i.e. an analogous DNA sequence, is obtainable from other microorganisms. For instance, the DNA sequence may be derived from another microorganism, in particular either a fungus or bacteria.

Such DNA sequences may originates from fungi, comprising a strain of an Aspergillus sp., in particular a strain of *A. aculeatus* or *A. niger*, a strain of Trichoderma sp., in particular a strain of *T. reesie, T. viride, T. longibrachiatum* or *T. koningii, T. harzianum* or a strain of a Fusarium sp., in particular a strain of *F. oxysporum*, or a strain of a Humicola sp..

Further a DNA sequence encoding a homologous enzyme may be expected to derive from bacteria, such as another strain of a Oerskovia sp., or a strain of an Arthrobacter sp., Cytophaga sp., Rhodothermus sp., in particular a strain of *Rh. marinus*, or a strain of a Clostrium, in particular strains of *Cl. thermocellum*, or a strain of Bacillus sp., in particular strains of *B. licheniformis., B. amyloliquefaciens*, or *B. circulars*.

Alternatively, the DNA coding for a β-1,3-glucanase of the invention may, in accordance with well-known procedures, conveniently be isolated from DNA from any of the above mentioned organisms by use of synthetic oligonucleotide probes prepared on the basis of a DNA sequence disclosed herein. For instance, a suitable oligonucleotide probe may be prepared on the basis of a partial nucleotide sequence of the sequence shown in SEQ ID No. 1.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the β-1,3-glucanase should be operably connected to a suitable promoter and terminator sequence. The promoter may be any DNA sequence which shows transcriptional activity in the host cell of choice and may be derived from genes encoding proteins either homologous or heterologous to the host cell.

It is preferred to use a vector under control of the promoter for the maltogenic β-1,3-amylase from *Bacillus stearothermophilus* and/or the signal of *Bacillus stearothermphilus*.

In a specific embodiment the expression vector comprises the plasmid pPFF1 shown in FIG. 1.

The procedures used to ligate the DNA sequences coding for the β-1,3-glucanase, the promoter and the terminator, respectively, and to insert them into suitable vectors are well known to persons skilled in the art (cf., for instance, Sambrook et al., Molecular Cloning. A Laboratory Manual, Cold Spring Harbor, N.Y., 1989).

The host cell which is transformed with the DNA sequence encoding the enzyme of the invention may be either eukaryotic cells or prokaryotic cells.

Suitable prokaryotic host cells are in particular bacterial cells.

Examples of such bacterial host cells which, on cultivation, are capable of producing the novel enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of Streptomyces, such as *S. lividans* or *S. murinus*, or gram-negative bacteria such as *Escherichia coli*. The transformation of the bacteria may be effected by protoplast transformation or by using competent cells in a manner known per se (cf. Sambrook et al., supra, 1989).

When expressing the enzyme in bacteria such as *E. coli*, the polypeptide may be retained in the cytoplasm, typically as insoluble granules (known as inclusion bodies), or may be directed to the periplasmic space by a bacterial secretion sequence. In the former case, the cells are lysed and the granules are recovered and denatured after which the polypeptide is refolded by diluting the denaturing agent. In the latter case, the polypeptide may be recovered from the periplasmic space by disrupting the cells, e.g. by sonication or osmotic shock, to release the contents of the periplasmic space and recovering the polypeptide.

In a specific embodiments of the invention the bacterial host cell is a strain of *Bacillus subtilis*, especially the strain *B. subtilis* DN1885 or the protease deficient strain *B. subtilis* ToC46.

Suitable eukaryotic cells are in particular fungal cells such as yeasts or filamentous fungal cells.

Examples of suitable yeast cells include cells of Saccharomyces spp., in particular strains of *Saccharomyces cerevisiae, Saccharomyces kluyveri, Sacchromyces uvarum,* or Schizosaccharomyces spp., such as *Schizosaccharomyces pombe.*

Methods for transforming yeast cells with heterologous DNA and producing heterologous polypeptides there from are described, e.g. in U.S. Pat. No. 4,599,311, U.S. Pat. No. 4,931,373, U.S. Pat. No. 4,870,008, U.S. Pat. No. 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931, 373. The DNA sequence encoding the polypeptide of the invention may be preceded by a signal sequence and optionally a leader sequence, e.g. as described above. Further examples of suitable yeast cells are strains of Kluyveromyces spp., such as *K. lactis,* or Hansenula spp., e.g. *H. polymorpha,* or Pichia spp., e.g. *P. pastoris,* Yarrowia spp., such as *Yarrowia lipolytica* (cf. Gleeson et al., J. Gen. Microbiol. 132, 1986, pp. 3459–3465; U.S. Pat. No. 4,882, 279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger.* The use of Aspergillus spp. for the expression of proteins is described in, e.g., EP 272 277, EP 238 023 and EP 184 438. The transformation of *F. oxysporum* may, for instance, be carried out as described by Malardier et al., Gene 78, p. 147–156, 1989.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g., by homologous or heterologous recombination.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

The expressed β-1,3-glucanase produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

In a still further aspect, the present invention relates to a novel enzyme preparation useful for the modification or degradation of β-glucan containing materials, said preparation being enriched in an enzyme exhibiting β-1,3-glucanase activity as described above.

The enzyme preparation having been enriched with the novel β-1,3-glucanase enzyme of the invention may e.g. be an enzyme preparation comprising multiple enzymatic activities, in particular an enzyme preparation comprising different enzyme activities required for the modification or degradation of microbial cell walls.

Examples of such enzyme preparations include lytic enzyme systems, in particular of microbial (fungal or bacterial) origin, e.g. derived from a strain of Trichoderma, such as *Trichodenna harzianum, Trichoderma viride* or *Trichodenna reesie,* a strain of Oerskovia sp., such as *Oerskovia xanthineolytica* (sometimes called *Cellulomonas cellelans*), a strain of Arthrobacter sp. such as *Arthrobacter luteus,* a strain of Rhizoctonia sp. or Cytophaga sp., a strain of a Staphylococcus sp., or a strain of Streptomyces sp..

Commercially available enzyme preparations which may conveniently be boosted with an enzyme of the invention includes Novozyme® 234 and Cereflo 200L, both available from Novo Nordisk A/S, Denmark, Cellulase (available from Merck), Cellulase CP and Cellulase CT (both available from Sturge), and/or Chitinase (available from Sigma), Zymolase from Kirin Breweries.

In the present context, the term "enriched" is intended to indicate that the β-1,3-glucanase activity of the enzyme preparation has been increased, e.g. with an enrichment factor of at least 1.1, conveniently due to addition of an enzyme of the invention prepared by the method described above.

Alternatively, the enzyme preparation enriched in an enzyme exhibiting β-1,3,-glucanase activity may be one which comprises an enzyme of the invention as the major enzymatic component, e.g. a mono-component enzyme composition.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to a β-1,3-glucanase of the invention, contain one or more other cell wall degrading enzymes, for instance those with cellulytic, mannanolytic, chitinolytic or proteolytic activities such as endo- and exoglucanase, mannanase, endo- and exochitinase, protease, or α- or β-mannosidase. The additional enzyme(s) may be producible by means of a microorganism belonging to the genus Aspergillus, preferably *Aspergillus niger, Aspergillus aculeatus, Aspergillus awamori* or *Aspergillus oryzae,* or the genus Trichoderma, or the genus Oerskovia, the genus Cytophaga, or the genus Arthrobacter or any of the microorganisms mentioned above in connection with the commercially available enzyme preparations.

Examples are given below of preferred uses of the enzyme preparation of the invention. The dosage of the enzyme composition of the invention and other conditions under which the composition is used may be determined on the basis of methods known in the art.

The enzyme preparation according to the invention is preferably used as an agent for degradation or modification of β-glucan containing material such as microbial cell walls. In particular, the enzyme preparation of the invention may be used for rupturing or lysing cell walls of microorganisms thereby enabling recovery of desirable products produced by the microorganism.

It will be understood that the specific composition of the enzyme preparation to be used should be adapted to the composition of the cell wall to be ruptured or lysed. For instance, yeast cell walls have been found to comprise two main layers, an outer layer of protein-mannan complex and an inner glucan layer. In order to efficiently rupturing the cell wall of yeast it is desirable that the enzyme preparation comprises at least protease, mannanase and β-glucanase activity.

The extract recovered after rupture of the microbial cell walls normally comprises a number of different components, such as pigments, vitamins, colorants and flavourants. Extracts obtained from rupture of yeast, i.e. yeast extracts, are used as such, e.g. for food or feed applications—or components thereof may be recovered and optionally further processed.

Examples of such products include vitamins, colorants (e.g. carotenoids, Q-10 and astaxanthin), enzymes, proteins and flavour components or flavour enhancers (e.g. MSG, 5'-GMP and 5'-EMP). The products to be recovered may be inherent products of the microorganism in question, or may be products which the microorganism has been constructed to produce, e.g. recombinant products.

In addition the enzyme preparation of the invention may be used in the production of protoplasts from yeasts (e.g. of Saccharomyces sp. or Schizosaccharomyces sp.) or from fungi (e.g. Aspergillus sp. or Penicillium sp.). Preparation and regeneration of protoplast from such organisms are important in fusion, transformation and cloning studies. The production of protoplasts may be performed in accordance with methods known in the art.

The invention may also be used for improving fungal transformation.

Further, the enzyme or enzyme preparation according to the invention may be used in the preparation of pharmaceuticals, especially products entrapped inside the cells in the cytoplasmic membrane, the peripiasmic space and/or the cell wall.

In addition, the enzyme preparation of the invention may be used in the modification of β-glucans such as curdlan and laminarin.

The invention is described in further detail in the following examples which are not in any way intended to limit the scope of the invention as claimed.

METHODS AND MATERIALS

Donor organism: *Oerskovia xanthineolytica* LLG109 (M. Lechevalier, Int. J. Sys. Bacteriol, 22(4), p. 260, 1972). *Oerskovia xanthineolytica* 73/14 (Shen et al., J. Biol. Chem, 266, p. 1058, 1991).

Deposited microorganisms:

*Oerskovia xanthineolytica* LLG109 strain has been deposited at the Deutshe Sammlung von Mikroorganismen und Zellkulturen GmbH., (DSM).

Deposit date: 13.10.95

Depositor's ref.: NN049107 (*Oerskovia xanthineolytica* LLG109)

DSM designation: *Oerskovia xanthineolytica* (or *Cellulomonas cellulans*) DSM No. 10297

Host organism.

*Bacillus subtilis* DN1885 (Diderichsen et al., Journal of Bacteriology, vol. 172, p. 4315–4321, 1990).

*Bacillus subtilis* protease deficient strain ToC46 (Diderichen et al., supra, 1990).

*E.coli* JM109 (Yanish-Perron et al., Gene 33, p. 103–199, 1985).

PF8A: *E. coli* JM109 harbouring plasmid pPF8A

PF15BK: *B. subtilis* DN1885 harbouring plasmid pPF15BK

PF11BgK: *B. subtilis* DN1885 harbouring plasmid pPF11BgK

PFF1: *B. subtilis* DN1885 harbouring plasmid pPFF1

Primers:

DS96: 5' cggaattccatgcctcacgacaggaggaa 3'

DS97: 5' tatggatccagatctcgtcgaagcacgtg 3'

Primers synthesized for the 5' region of the yeast lytic 57 KDa β-1,3-glucanase from *O. xanthineolytica* 73/14.

DS121: 5' ccN ggN gaY YtN YtN tgg 3'

DS141: 3' atR gtY ggN gtY atR cc 5'

DS140: 5' ttY gtN gaY ggN caR caR tt 3'

DS142: 3' aaR caN ctR ccN gtY gtY aa 5'

DS143: 3' ctR atR caN KcN caN atR ct 5'

Y=C or T

R=A or T

K=G or T

N=C, T, AorG

Synthesized according to known amino acid sequences of the β-1,3-glucanase (Ventom and Asenjo, supra, 1991).

DK15: 5' cgtactcggggggtggcttcagcggcgtttggattgtac 3'

AvaI

DK16: 5' gatgcaagcttgcattacgaaaggagac 3'

HindIII

Primers used for plasmid pDN1777 DNA amplification by PCR. Double underlined nucleotide sequences correspond to *B. stearothermophilus*, whereas the underlined nucleotide sequence correspond to *O. xanthineolytica* LLG109.

Figure 2:
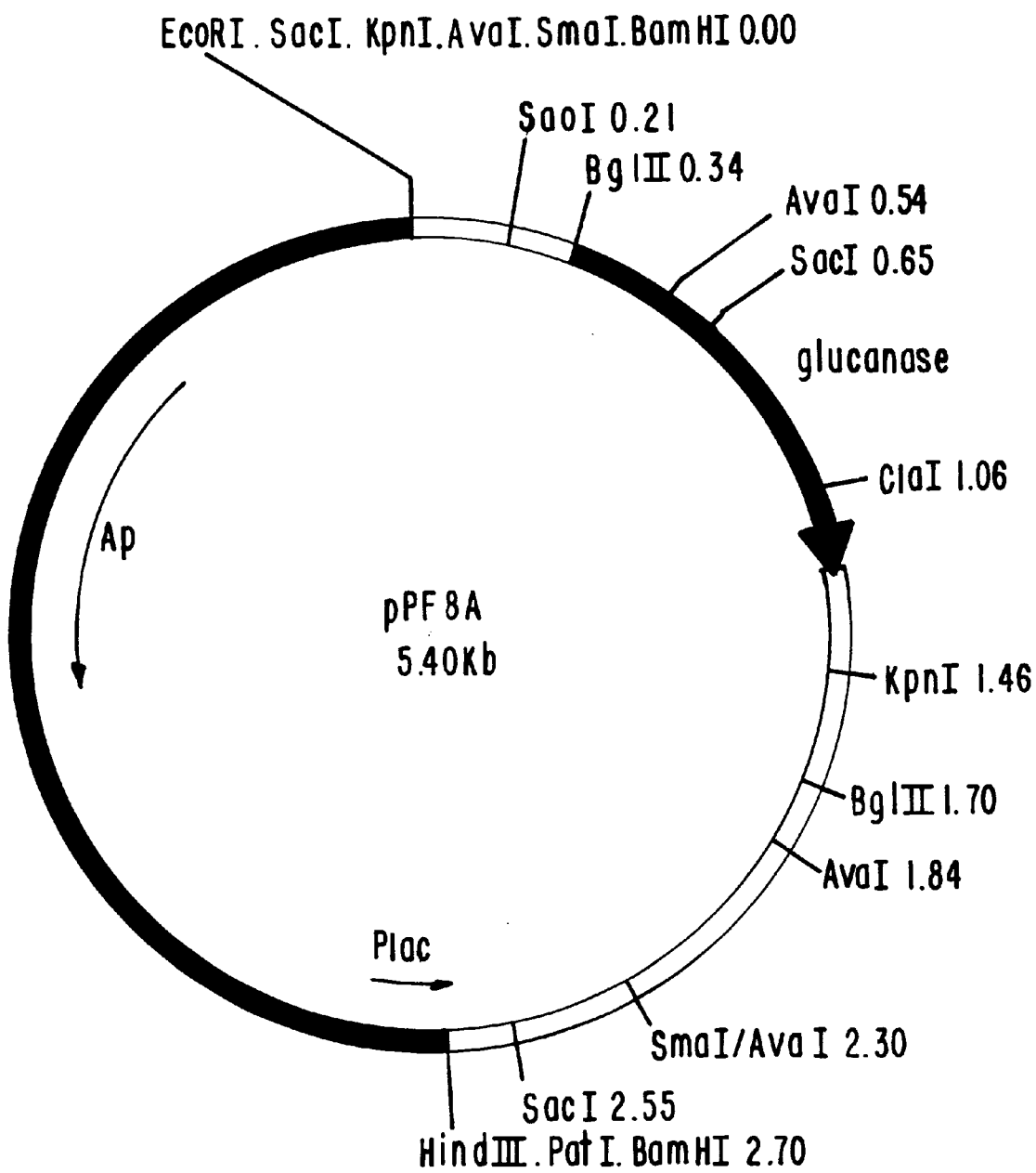
FIG. 2 shows the map of plasmid pPF8A.

Plasmids:

pPRFF1: See FIG. 1 pPF8A: 2.7 Kb BamHI-BamHI fragment from *O. xanthineolytica* LG109 (see FIG. 2). PpDN520: (Diderichsen, B. and Christiansen, L., FEMS Microbiology Letters 56, p. 53–60, 1988).

pUC18: (Yanish-Perron, C., Viera, J and Messing, J., Gene, 33, p. 103–199, 1985)

pDN2801: (Diderichsen, B., Wested, U., Hedegaard, L., Jensen, B. R. Sjohølm, C., Journal of Bacteriology, Vol. 172, p. 4315–4321, 1990).

Promoter:

Maltogenic α-amylase from *Bacillus stearotherophilus* (Diderichen et al., supra, 1988)

METHODS

Isolation of genomic DNA: Chromosomal DNA from *O. xanthineolytica* was prepared according to Meade et al., J. Bacteriol., 149(1), p. 114–122, 1982).

Construct of a genomic DNA partial library for *O. xanthineolytica* LLG109. Chromosomal DNA from *O. xanthineolytica* LLG109 was partially digested with BamHI. The digested DNA was fractionated by agarose gel electrophoresis. Fragments with sizes of about 1.6 to 4 kb were isolated and purified. The resulting BamHI fragments were mixed with BamHI-digested-Bacterial Alkaline dephosphorilated pUC18 plasmid vector (pUC18 BamHI/BAP from Pharmacia), and ligate with T4 ligase (BRL). This ligation mixture was used to transform electrocompetent *E. coli* JM109 cells by electroporation (Bio-Rad Gene Pulser; 125

μFD capacitance, 200Ω Resistance). E coli JM109 cells were made competent according to Sambrook et al., "A laboratory manual, Cold Spring Harbor Laboratory Press, New York,, 1989.

Screening of the partial DNA library from O. xanthineolytica LLG109 with radiolabelled DS140/DS143 PCR product: The partial DNA library from strain LLG109 was plated in a total of 11 plates (with about 50 white (recombinant) colonies/plate). The library was replicated on sterile nylon membranes (Hybond-N, Amersham) as described by Sambrook, supra, 1989). The replica membranes were probed with the radiolabelled PCR product according to Sambrook et al., supra, 1989, under the following conditions: Hybridization temperature: 65° C., hybridization solution (100 ml) 6XSSC, 0.5% non-fat dried milk. Hybridization was carried out overnight (18 hours). After hybridization, filters were washed as follows: 10 min+15 min in 200 ml of 2×SSC at 65° C. and 5 min at 65° C. in 0.2×SSC, 0.1% SDS. Filters were subjected to autoradiography (Fuji Film) overnight as −70° C. to detect $^{32}$P-labelled probe on filter.

(Poymerase Chain Reaction) Amplification:

PCR amplification from O. xanthineolytica LLG109

The PCR reactions were carried out using 100 pmols of each degenerate primer per reaction. An amount of 100 ng of Oerskovia DNA was used per reaction. Taq DNA Polymerase from Promega was used using the conditions recommended by the manufacturer. Cycling conditions were as followed: Hot start: 95° C. for 1 minute 40 cycles.

The PCR product was cloned in pUC18/SmaI as described by Kanungo and Pandey, Biotechniques, 14(6), p. 912, 1993, for subsequent sequencing.

Gel electrophoresis of DNA and Southern Blotting

Agarose gel electrophoresis, and Southern Blotting, was used to analyze plasmids, restriction endonuclease fragments, ligation products, PCR reaction, according to Sambrook et al., supra, 1989.

Recovery of DNA from agarose gels was done according to Sambrook et al., supra, 1989.

Radiolabelling of double-stranded DNA fragments.

Radiolabelling of double-stranded DNA fragments was done according to Sambrook et al., supra, 1989.

DNA hybridization experiments.

Hybridization of Southern blots on nylon filters (Hybond-N, Amersham) with $^{32}$P-labelled PCR probe were carried out following methods described by Sambrook et al., supra, 1989. The hybridization conditions were as follows: Hybridization temperature: 65° C. Hybridization solution: 6×SSC, 0.5% non-fat dried milk). The hybridization solution was carried out overnight.

Transformation of E. coli:

Cells of E. coli were transformed by electroporation as described in the manual for the BIO-RAD Gene Pulser electroporation apparatus.

Transformation of B. subtilis:

Competent cells were prepared and transformed as described by Yasbin, R. E., Wilson, G. A. and Young, F. E., J. Bacteriol. vol. 121, p. 296–304, 1975.

Identification of positive clones:

The identification was done according to Sambrook et al., supra, 1989.

DNA sequencing

DNA sequencing was done using the same SEQUENASE sequencing kit from USED following the manufactures recommendations. DNA compressions were resolved by using the reagent kit for DNA sequencing using 7-deaza-dGTP and sequenase (also from USBI).

Isolation of plasmid DNA:

E. coli: The isolation of E. coli plasmid was performed according to Sambrook et al., supra, 1989, using the method described in Promega Protocols and Application Guide).

B. subtilis: The isolation of B. subtilis was done as described by Kieser, T., Plasmid, 12, p. 19–36, 1984.

Immunological cross-reactivity: Antibodies to be used in determining immunological cross-reactivity may be prepared by use of a purified β-1,3,-glucanase. More specifically, antiserum against the β-1,3-glucanase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, p. 655–706), by crossed immunoelectrophoresis (N. Axelsen et al., supra, Chapters 3 and 4), or by rocket immunoelectrophoresis (N. Axelsen et al., Chapter 2).

| Media | | |
|---|---|---|
| LB agar | | |
| Bacto-tryptone | 10 | g/l |
| Bacto yest extract | 5 | g/l |
| NaCl | 10 | g/l |
| Bacto agar | 15 | g/l |
| adjusted to pH 7.5 with NaOH | | |
| All autoclaved at 121° C., 30 minutes. | | |

LBGP agar

LB agar containing 10 mM potassium phosphate pH 7.0, 0.4% glucose. All autoclaved at 121° C. for 30 minutes.

| Jacm-7-medium: | | |
|---|---|---|
| Maltodextrin 02 | 40 | gram |
| (average chain length = 12) | | |
| Sucrose | 20 | gram |
| $MgSO_4 \cdot 7H_2O$ | 0.64 | gram |
| $KH_2PO_4$ | 10 | gram |
| $Na_2HPO_4 \cdot 2H_2O$ | 10 | gram |
| Mikrosoy | 10 | ml |
| Tapwater at | 1 | liter |
| pH adjusted to 7.0 with NaOH | | |

The nitrogen sources, Casitone and $(NH_4)_2HPO_4$ were added separately after autoclaving as concentrated solutions, the final concentrations were:

| | | |
|---|---|---|
| Casitone | 9.6 | gram/l |
| $(NH_4)_2HPO_4$ | 10.8 | gram/l |
| All autoclaved at 121° C. for 60 minutes. | | |
| Fermentation broth-1: | | |
| Casitone | 152 | gram |
| $KH_2PO_4$ | 5.16 | gram |
| $Na_2HPO_4 \cdot 2H_2O$ | 5.12 | gram |
| $K_2SO_4$ | 1.09 | gram |

-continued

| | | |
|---|---|---|
| MgCl$_2$,6H$_2$O | 1.11 | gram |
| Lic-tracemetals | 20 | ml |
| Antifoam SB2121 | 1 | ml |
| (Struktol SB2121 from Schill & Seilacher GmbH, Hamburg, Germany) | | |

The volume was adjusted to 1.0 liter with tap water. The pH was adjusted to 5.0 with H$_3$PO$_4$ before sterilization in an autoclave at 121° C. for 60 minutes.

| | Content in 1 litre flask: | |
|---|---|---|
| Sucrose feed solution: | | |
| MgCl$_2$,6H$_2$O | 8.08 | gram |
| Lic-tracemetals | 34 | ml |
| Antifoam SB2121 | 1.3 | ml |
| Sucrose | 241 | gram |
| Tapwater to | 500 | ml |
| Also autoclaved at 121° C. for 60 minutes. | | |
| CAL 18-2 medium: | | |
| Yeast extract | 40.0 | gram |
| MgSO$_4$ | 1.3 | gram |
| Maltodextrin 02 | 50.0 | gram |
| NaH$_2$PO$_4$ | 20.0 | gram |
| Trace metals 1 | 6.67 | ml |
| Deionized water to | 1 | liter |

The pH was adjusted to 6.0 with NaOH and autoclaved at 121° C. for 60 minutes.

| TRACE METAL SOLUTIONS | |
|---|---|
| Mikrosoy: | mg/l |
| MnSO$_4$,H$_2$O | 500 |
| FeSO$_4$,7H$_2$O | 2000 |
| CuSO$_4$,5H$_2$O | 200 |
| ZnCl$_2$ | 200 |
| Na$_2$B$_4$O$_7$,10H$_2$O | 1000 |
| BaCl$_2$,2H$_2$O | 100 |
| (NH$_4$)$_6$Mo$_7$O$_{24}$,4H$_2$O | 100 |
| Na$_3$-citrat,H$_2$O | 10,000 |
| All autoclaved at 121° C. for 60 minutes. | |
| Mikrosoy: | mg/l |
| MnSO$_4$,H$_2$O | 500 |
| FeSO$_4$,7H$_2$O | 2,000 |
| CuSO$_4$,5H$_2$O | 200 |
| ZnCl$_2$ | 200 |
| Na$_2$B$_4$O$_7$,10H$_2$O | 1000 |
| BaCl$_2$,2H$_2$O | 100 |
| (NH$_4$)$_6$Mo$_7$O$_{24}$,4H$_2$O | 100 |
| Na$_3$-citrat,H$_2$O | 10,000 |
| All autoclaved at 121° C. for 60 minutes | |
| Trace metals 1: | |
| MnSO$_4$ | 4.48 g |
| FeCl$_3$,6H2O | 3.33 g |
| CuSO$_4$,5H$_2$O | 0.625 g |
| ZnSO$_4$,7H$_2$O | 7.12 g |
| Na$_2$MoO$_4$ | 2.0 g |
| KI | 1.0 g |
| Deionized water to | 1 liter |
| Lic-tracemetals: | mg/l |
| MnSO$_4$,H$_2$O | 500 |
| FeSO$_4$,7H$_2$O | 2000 |
| CuSO$_4$,5H$_2$O | 200 |
| ZnCl$_2$ | 200 |
| All autoclaved at 121° C. for 60 minutes. | |

Enzymes:
Native β-1,3-glucanase from *Oerskovia xanthineolytica* LLG109 (Ventom and Asenjo, Enzyme Microb. Technol., 13, p. 71, 1991).
Substrate:
AZCL-curdlan: Megazyme, Sydney, Australia
Laminarin: Sigma
Enzyme assay:
Assay conditions:
Shaking waterbath, 37° C. for 1 hour.
Incubation mixture: 0.5 ml supernatant+0.5 ml 1 w/v% AZCL-curdlan+0.5 ml acetate-buffer (pH 4.0). Curdlan was also dissolved in the acetatebuffer. The reaction was stopped with 3 ml of stop reagent. The insoluble curdlan was spun down by centrifugation and the dissolved blue coloured part determined on a Hitachi Spectrophotometer at 590 nm, 1 cm.

| Stop reagent: | | |
|---|---|---|
| Sodiumacetate | 40 | gram |
| Zinkacetate | 4 | gram |
| Deionized water to | 200 | ml |

The pH was adjusted to 5.0 before mixing with 800 ml of 2-methoxyethanol.

EXAMPLES

Example 1

PCR amplification of native genomic DNA from *O. xanthineolytica* LLG109.

Native genomic DNA from *O. xanthineolytica* was prepared as described above and amplified using PCR technic.

Primers DS96 and DS97 were synthesized for the 5' region of the yeast-lytic 57 kDa , β-1,3-glucanase gene from *O. xanthineolytica* LLG109 starting from the putative start codon and for the 3' region just downstream from the putative stop codon. Bases for sequences for EcoRI and BamHI were introduced at the 5' primer (DS96) and 3' primer (DS97).

PCR amplification from genomic DNA from strain *O. xanthineolytica* LLG109 using these primers gave a 1.7 kb DNA fragment. The PCR-fragment was checked by digesting it at various restriction sites internal to the gene.

Example 2

Partial amino acid sequence determination from the 26 kDa lytic β-1,3-glucanase from *O. xanthineolytica* LLG109

The following amino acid sequences were initially obtained from the N-termninal of the native β-1,3-glucanase and from peptides generated by trypsin digestion of the native enzyme. Proteolytic digestion, peptide separation and amino acid sequencing were done according to standard procedures.
N-Terminal native enzymne:
N-Ala-Pro-Gly-Asp-Leu-Leu-Trp-Xaa-Asp-Glu-Phe-
Peptide 1:
Tyr-Gln-Pro-Gln-Tyr-Gly-Arg-Ile-Glu-Ala—Arg-Ile-Gln-Pro-Arg-Gly-
Peptide 2:
Phe-Val-Asp-Gly-Gln-Gln-Phe-Xaa-Arg-Val-
Peptide 3:
Val-Asp-Tyr-Val-Arg-Val-Tyr-Asp- Example 3.

*O. xanthineolytica* LLG109 chromosomal DNA amplification by PCR.

Chromosomal DNA from *O. xanthineolytica* LLG109 was amplified by PCR using different combinations of the mixed oligonucleotides synthesized on the basis of reverse translation of amino acid sequence from β-1,3-glucanase.

PCR reaction using primer DS140 (reverse sense translation of the amino acid sequence FVDGQQF from peptide 2) and DS143 (reverse antisense translation of the amino acid sequence DYVRVY from peptide 3) produced a 180 bp DNA fragment. This PCR product was subsequently cloned into pUC18 and transformed into *E. coli* JM109 in order to determine its complete nucleotide sequence (see SEQ ID No. 3).

Example 4

Southern blot hybridization analysis of chromosomal DNA from strain LLG109 using DS140/DS143 PCR product as a probe.

Chromosomal DNA from strain LLG109 was analyzed by Southern blotting using the radiolabelled DS140/DS143 PCR product as a probe under stringent conditions. A strong positive signal from BamHI—BamHI band of approximately 2.65 kb or from an about 8 kb KpnI—KpnI band or a 1.5 Kb BamHI-KpnI band.

In contrast, the PCJR probe strongly hybridised (under the same conditions) to either a 8 kb BamHI-BamHI band, a 8 kb KpnI—KpnI band or an about 5 kb BamHI-KpnI band in Southern blot hybridization analysis of chromosomal DNA from Strain 73/14. In both cases, the pattern of bands, in the Southern blots from both Oerskovia strains showing strong hybridization to the radiolabelled probe, was different to that observed using the PCR product DS133/DS135.

Therefore, it was concluded that both *O. xanthineolytica* strain LLG109 and 73/14 probably had at least two different β-1,3-glucanase genes.

Example 5

Cloning of 26 kDa β-1,3-glucanase gene from *O. xanthineolytica* LLG109 in *E. coli*.

In order to clone the 2.7 kb BamHI-fragment hybridizing to the DS140/DS143 PCR-probe, appropriate sized (2.7 kb+/−0.5 kb) BamHI DNA-fragments from the chromosome of strain LLG109 were purified and ligated to the BamHI site of pUC18. *E. coli* JM109 was transformed by electroporation with the ligates and screened by colony hybridization using the same DS140/143 PCR-probe and conditions mentioned above.

A clone from the partial gene bank harbouring recombinant plasmid pPF8A was isolated. This plasmid was mapped by restriction enzyme analysis.

Location of the region of the plasmid homologous to the DS140/DS143 PCR-probe and insert orientation was determined by Southern blotting. Plasmid pPF8A contained 2.7 kb BamH1 insert. In the plasmid the probe was hybridizing to the 1.5 kb BamHI-KpnI fragment contained in the 2.7 kb BamHI insert. This fact was consistent with the genomic Southern blot hybridization result using DS140/DS143 PCR probe.

Example 6

Nucleotide sequence of the 3-1,3-glucanase gene.

The nucleotide sequence of the 1.5 kb BamHI-KpnI fragment from pPF8A was determined by the Dideoxi Chain Termination method. Double-stranded DNA was denaturated by alkali or heat treatment before using it as a template for sequencing reactions. Both strands of this region from pPF8A were sequences according to the sequence strategy shown.

The complete nucleotide sequence of the 1.5 kb BamHI-KpnI fragment and the deduced amino acid sequence are shown in SEQ ID No. 1 below.

The nucleotide sequence contains an Open Reading Frame (ORF) of 921 nucleotides encoding a protein composed of 306 amino acids. Amino acid sequences identical or very similar to those existing in the native protein were present along the amino acid sequence predicted from the DNA sequence (amino acid residues different are discussed below). The codon ATG is used as initiation codon in this OFR. A putative Ribosome Binding Site (RBS) is present 4 nucleotides upstream the initiation codon. Upstream of this ORRF, there are two other in-frame ATG codons (nucleotides 321 and 351). However, it is unlikely that any of these functions as an initiation codon, because none of them are preceded by putative RBS's in the expected positions. Computer scanning of the sequence upstream of the coding region could not find sequences compatible with an *E. coli* type of promoter. In the 3'-flanking region, which is downstream the termination codon TGA, there is a G+C-rich region (69% C+G) 13 base pairs inverted repeat sequence. This sequence can make a stem-loop structure and possibly may function as a transcription termination signal. The 1.5 kb BamHI-Kpn1 DNA fragment has a G+C content of 67%, and the G+C content of the ORF was, similar to that of Oerskovia chromosomal DNA reported previously (70–75% G+C) (Stackebrandt and Prauser, System. Appl. Microbiol., 14, p. 261–265, 1991).

Amino acid sequence of the precursor of the β-1,3 glucanase

The ORF of the β-1,3 glucanase gene encode a 306 amino acid protein. The $NH_2$-terminal end of the deduced amino acid sequence exhibits signal sequence characteristics found in other secreted proteins (von Heine, Nucl. Acids Res., 14(11), p. 4683, 1986). Following the initiation codon there are three positive charged amino acid residues (histidine 5 and arginine 12 and 13) which are trailed by a long stretch of hydrophobic amino acid ($Leu^{17}$-$Ala^{23}$ and $Ala^{26}$-$Ala^{35}$). The computer prediction for prokaryotic secretory signal sequence gave the following positions as best potential cleavage sites: i) potential cleavage site between position 35 and 36. The $NH_2$-terminal sequence of the native mature form of β-1,3-glucanase purified by Ventom and Asenjo, supra, 1991, from strain LLG109 fermentation broth was determined as APGLLWSDEFDGAAGS. This amino acid sequence shows a high similarity to that predicted from the nucleotide sequence in positions $Thr^{64}$-$Ser^{80}$: TPESLAWS-DEFDGAAGS. Amino acid differences (see FIG. 3) observed between the predicted amino acid sequence and the sequence obtained from the native β-1,3-glucanase (underlined amino acid residues) suggest that the ORF found in pPF8A may code for a different β-1,3-glucanase, an isoenzyme to the enzyme described by Ventom & Asenjo, supra, 1991. As a result, the amino acid residue $Thr^{64}$ forms a $NH_2$-terminal end of the β-1,3-glucanase isoenzyme. Hence, the peptide containing 63 amino acids ($Met^1$-$Val^{63}$) should be considered as a prepro-region. The molecular weight of the mature β-glucanase ($Thr^{64}$-$Gln^{243}$) was calculated to be 26.278, which is similar to that previously calculated from SDS-PAGE by Ventom and Asenjo, supra, 1991, for the characterized β-1,3-glucanase. The predicted pI for this new enzyme is 3.77, which is so much lower than the previously reported (Ventom and Asenjo, supra, 1991) pI of 5.0, that no doubts can be left that a new hitherto unknown β-glucanase was found.

Example 7

Cloning and expression of the 26 kDa β-1,3-glucanase gene in *Bacillus subtilis*

Figure 4:
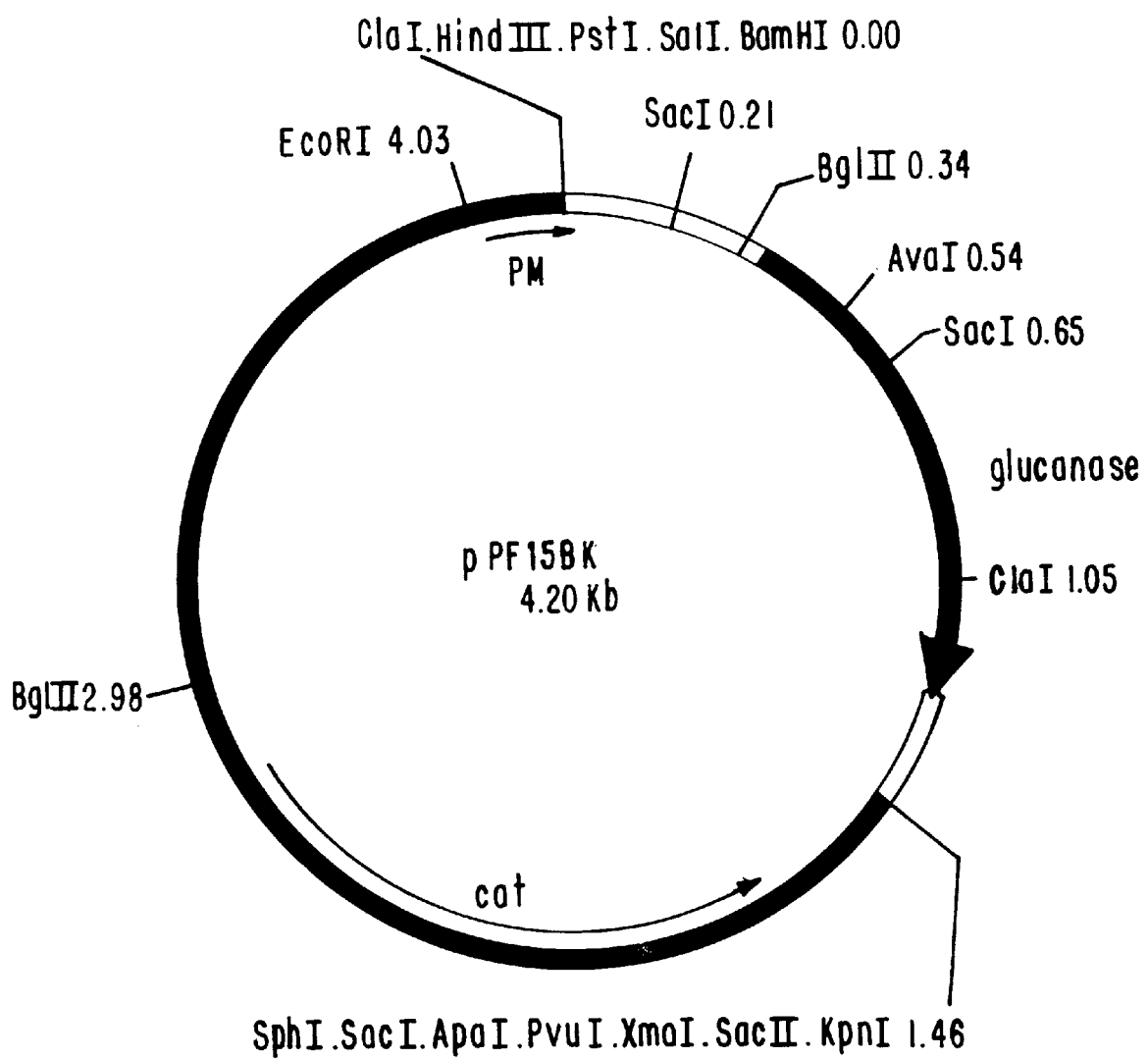
FIG. 4 shows the map of plasmid pPF15BK.
Figure 5:
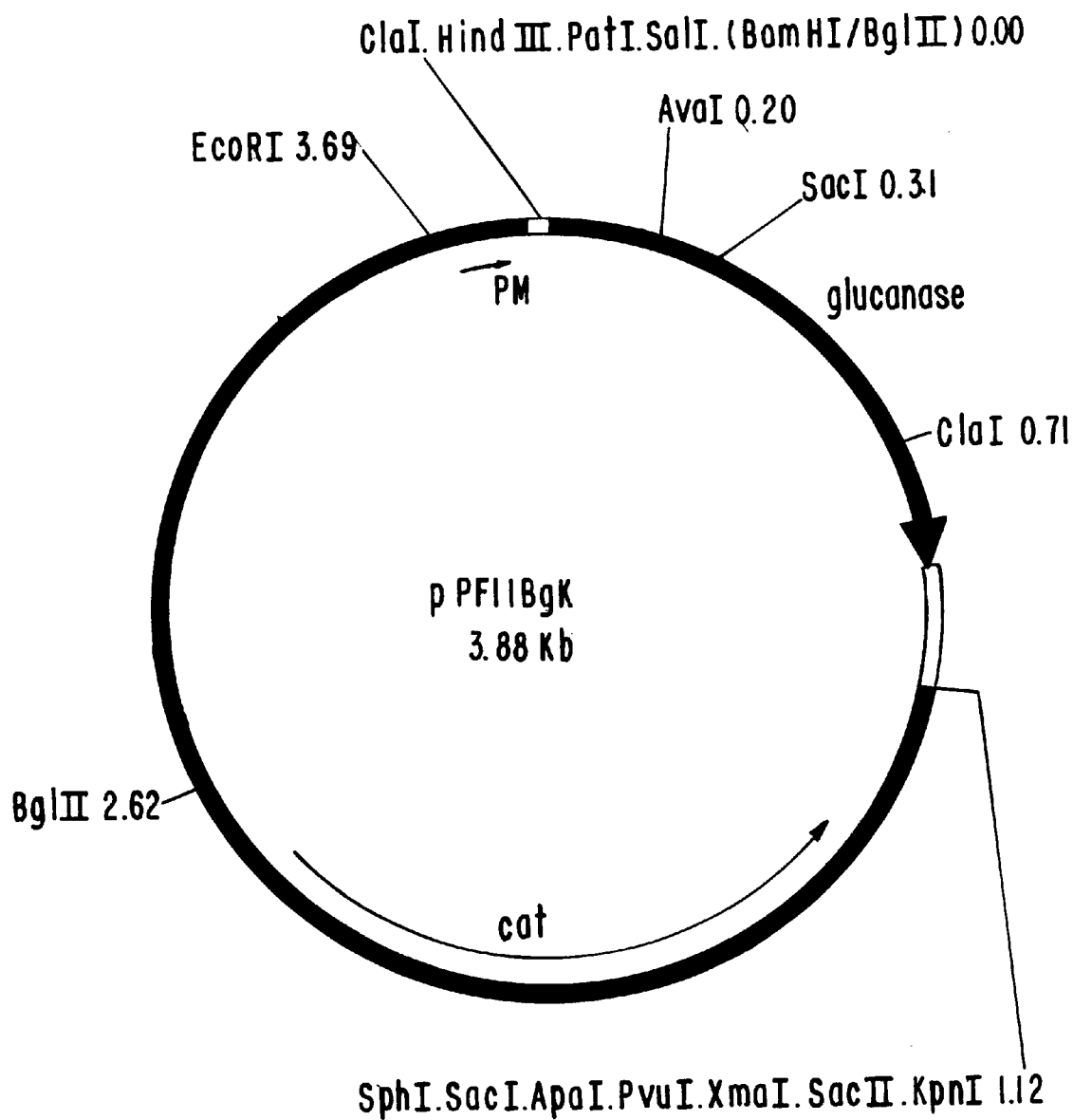
FIG. 5 shows the map of plasmid pPF11BgK.

The 1.5 kb BamHI-KpnI fragment from pPF8A was cloned in *B. subtilis* DN1885 on plasmid pDN2801 under the control of the promoter for the maltogenic α-amylase from *B. stearotherophilus* (Diderichsen, supra, 1990) producing the plasmid pPF15BK (FIG. 4). The 1.1 kb BglII-KpnI fragment contained in the 1.5 kb BamHI-KpnI fragment was cloned in the same way to give pPF11BgK (FIG. 5). However, neither plasmid transformed (Yasbin et al., J. Bacteriol. 12, p. 296–304, 1975) into *B. subtilis* DN1885 gave rise to any detectable β-1,3-glucanase activity on LBGP agar plates containing AZCL-curdlan nor in liquid culture (CAL 18-2, 3 days, 30° C., 250 rpm) supernatants. Alternatively, expression of the β-glucanase gene was performed by replacing the native expression signals with those from the well-expressed *Bacillus stearothermophilus* gene mentioned above. A perfect fusion of the nucleotide sequence for the promoter, RBS and signal peptide of the maltogenic α-amylase gene from *B. stearothermophilus* and the codons for Thr64 and the rest of the β-1,3-glucanase ORF, including the terminator, was made. This final construct pPFF1 was made as follows: A 0.2 kb HindIII-AvaI fragment from pPF11BgK was replaced by a 0.15 kb HindIII-AvaI fragment made by PCR. The PCR fragment contained the RBS and the signalpeptide coding regions of the *B. stearothermophilus* maltogenic α-amylase. The PCR fragment was obtained following pDN520 (Diderichsen et al., supra, 1988) DNA amplification using primers DK15 and DK16. Plasmid pPFF1 was finally transformed into *B. subtilis* DN1885 (Yasbin et al, supra, 1975). In this case β-1,3-glucanase activity could be detected after 24 hours, 37° C. on laminarin (0.04%) containing LE agar plates after staining with congo red. Finally pPFF1 was transformed into the protease deficient host *B. subtilis* ToC46.

Example 8
Fermentation and production of β-1,3-glucanase from *Bacillus subtilis* DN1885/pPFF1.

The strain *Bacillus subtilis* DN1885/pPFF1 was grown in a 2 liter fermentation vessel supplied with a magnetic coupled stirrer drive, pH- and temperature control and a peristaltic pump to add the carbon source at fixed rates. 100 μl of the −80° C. stock culture of strain DN1885/pPFF1 was used to inoculate a 500 ml shakeflask containing 100 ml of Jacm-7-broth and 1 mg of chloramphenicol and propagated for 24 hours at 250 rpm and 30° C. on a rotating table. This culture (pH=7.3 and $OD_{600}$=22) was used to inoculate the fermenter already containing 1.0 liter Fermentation broth 1. Biomass growth and enzyme formation Before inoculation of the culture as described above, 32 gram of the Sucrose solution was added to the fermenter. Also sterile filtered air was sparged into the fermenter at the bottom drive at a rate of 1 liter/minute. The stirrer speed was at the beginning set to 500 rpm, but automatically coupled to the dissolved oxygen tension signal at a set point of 20% DOT (Dissolved Oxygen Tension). A peristaltic Watson-Marlow pump was used to feed the Sucrose feed solution with a constant rate of 7.1 gram/hour after 10 hours of growth, this forced the stirrer to run close to the maximum value of 1100 rpm and brought the DOT close to 0. After 19 hours we therefore reduced the sucrose feed rate to ~6.0 gram/hour, which was kept until the bottle was emptied after ~82 hours fermentation time. The fermentation was stopped after 93 hours, cooled down to 4° C. and stored for later recovery.

The temperature was controlled at 34.0° C. +/− 0.1¢C., pH to 6.00 +/− 0.10 by addition of diluted ammonia in water or 5 v/v% $H_3PO_4$.

Samples were taking daily and pH, dry weight biomass and β-1,3-glucanase activity determined as described in the section Materials and Methods. Enzyme concentrations in the culture supernatants were determined by AZCL-curdlan hydrolysis. Fermentation results shown in Table 1.

TABLE 1

| Fermentation, hours | Dry weight Biomass, gram/l | Activity, $OD_{590}$ | pH | RPM |
| --- | --- | --- | --- | --- |
| 0 | nd | nd | 5.24 | 499 |
| 18.7 | 21.3 | nd | 6.09 | 1065 |
| 43.0 | 23.6 | 0.564 | 6.10 | 835 |
| 70.3 | 27.3 | 0.676 | 6.10 | 901 |
| 93.0 | 26.1 | 0.761 | 6.10 | 499 | nd = not determined

Example 9
Growth and enzyme expression on CAL 18-2 medium.

The strain *B. subtilis* DN1885/pPFF1 was grown on LB agar plates containing 10 μg/ml Chloramphenicol for 3 days at 30° C. A single colony was transferred to a 500 ml shakeflask containing 100 ml of CAL 18-2 medium and 1 mg of chloramphenicol. Growth was propagated at 30° C., on a rotating table at 250 RPM, for 3 days. Samples were taken every day and activity, pH, $OD_{600}$ and dry weight biomass determined. The activity determination was made as described in the section Methods and Materials, except that we used 0.05 ml supernatant+0.25 ml curdlan+0.2 ml water and stopped with 2 ml of stop reagent. Also the incubation time was extended to 20 hours.

Results are displayed in Table 2.

TABLE 2

| Fermentation, days | $OD_{600}$ | Dry weight biomass, g/l | β-glucanase Activity, $OD_{590}$ | pH |
| --- | --- | --- | --- | --- |
| 1 | 16.5 | 4.6 | 0.033 | 6.52 |
| 2 | 40.6 | nd | 0.296 | 7.06 |
| 3 | 40.5 | 11.5 | 0.709 | 7.34 | nd = not determined

Example 10
N-terminial amino acid sequence determination and mass spectrometry of purified recombinant β-1,3-glucanase.

The fermentation broth containing the recombinant β-1, 3-glucanase was ultrafiltrated and washed with 20 mM Tris-HCl pH 8.5 in a Filtron concentrator equipped with a Minisette 10 kDa membrane. The sample was applied on a Q-Sepharose column equilibrated with 20 mM Tris-HCl pH 8.5 and the β-1,3-glucanase was eluted with a linear gradient from 0 to 1M NaCl in 10 column volumes. The fractions containing β-1,3-glucanase activity were pooled. The pool was made 1.7M with respect to ammonium sulfate and pH was adjusted to 6.5. The pool was further purified on a Phenyl-Sepharose column equilibrated with 30 mM MOPS containing 1.7M ammonium sulfate pH 6.5. Elution of the β-1,3-glucanase was performed with 10 mM Tris-HCl pH 8.5 using a linear gradient in 10 column volumes. The fractions containing β-1,3-glucanase activity were pooled and dialyzed extensively against 10 mM sodium borate pH 9.0. The dialyzed sample was applied on a Mono Q column equilibrated with 10 mM sodium borate and the β-1,3-glucanase was eluted with a linear gradient from 0 to 1M NaCi in 40 column volumes.

The N-terminal amino acid sequence of the purified recombinant β-1,3-glucanase is identical to the N-terminal sequence deduced from the SEQ ID No. 1.

Matrix assisted laser desorption ionisation time-of-flight mass spectrometry of the purified recombinant β-1,3-glucanase gave a mass of 26 462 Da which within the experimental error is in accordance with the mass calculated from the amino acid sequence.

---

ABBREVIATIONS

AMINO ACIDS

| | | | | |
|---|---|---|---|---|
| A | = | Ala | = | Alanine |
| V | = | Val | = | Valine |
| L | = | Leu | = | Leucine |
| I | = | Ile | = | Isoleucine |
| P | = | Pro | = | Proline |
| F | = | Phe | = | Phenylalanine |
| W | = | Trp | = | Tryptophan |
| M | = | Met | = | Methionine |
| G | = | Gly | = | Glycine |
| S | = | Ser | = | Serine |
| T | = | Thr | = | Threonine |

-continued

ABBREVIATIONS

| | | | | |
|---|---|---|---|---|
| C | = | Cys | = | Cysteine |
| Y | = | Tyr | = | Tyrosine |
| N | = | Asn | = | Asparagine |
| Q | = | Gln | = | Glutamine |
| D | = | Asp | = | Aspartic Acid |
| E | = | Glu | = | Glutamic Acid |
| K | = | Lys | = | Lysine |
| R | = | Arg | = | Arginine |
| H | = | His | = | Histidine |

NUCLEIC ACID BASES

| | | |
|---|---|---|
| A | = | Adenine |
| G | = | Guanine |
| C | = | Cytosine |
| T | = | Thymine (only in DNA) |
| U | = | Uracil (only in RNA) |

---

We claim:

1. A DNA construct comprising a DNA sequence encoding an Oerskovia β-1,3-glucanase activity, wherein the DNA sequence is selected from the group consisting of:
(a) the DNA sequence of SEQ ID NO:1;
(b) a DNA sequence encoding the amino acid sequence encoded by the DNA sequence of SEQ ID NO:1; and
(c) a DNA sequence which hybridizes with the DNA sequence of SEQ ID NO:1 under conditions of: hybridization in a solution of 6×SSC, 0.5% non-fat dried milk with 100 μM ATP for 18 hrs. at about 65° C., followed by a first wash in 2×SSC at a temperature of about 65° C., and a second wash 5 min in 0.2×SSC, 0.1% SDS at a temperature of about 65° C.

2. The DNA construct of claim 1, comprising the DNA sequence of SEQ ID NO:1.

3. A DNA construct of claim 1, wherein the DNA sequence is derived from Oerskovia xanthineolytica.

4. A DNA construct of claim 3, wherein the DNA sequence is derived from Oerskovia xanthineolytica LLG109 (DSM No. 10297).

5. A DNA construct comprising a DNA sequence encoding an enzyme exhibiting β-1,3-glucanase activity, wherein the DNA sequence is selected from the group consisting of:
(a) a DNA sequence encoding an amino acid sequence having the sequence of SEQ ID NO:2;
(b) a DNA sequence encoding a modified amino acid sequence of (a), wherein one or more amino acids are substituted or deleted and wherein said modified amino acid sequence retains β-1,3-glucanase activity.

6. A recombinant expression vector comprising the DNA construct of claim 1.

7. The recombinant expression vector of claim 6, wherein the vector comprises the maltogenic α-amylase promoter from B. stearothermophilus.

8. The recombinant expression vector of claim 6, wherein the vector comprises the maltogenic α-amylase signal from B. stearothermophilus.

9. The recombinant expression vector of claim 6, comprising a sequence from the pPFF1 plasmid.

10. A cell comprising the DNA construct of claim 1.

11. The cell of claim 10, wherein the cell is a microbial cell or a bacterial cell.

12. The cell of claim 11, wherein the cell is a bacterial cell selected from the group consisting of Oerskovia, Arthrobacter, Cytophaga, Rhodothermus, Bacillus, Streptomyces, or Escherichia.

13. The cell of claim 12, wherein the bacterial cell is *Bacillus subtilis* DN1885 or *Bacillus subtilis* ToC46.

14. The cell of claim 10, wherein the cell is a fungal cell selected from the group consisting of a strain of Aspergillus, Trichoderma, Fusarium, or and Humicola.

15. A method of producing an enzyme exhibiting β-1,3-glucanase activity, comprising culturing the cell of claim 10 under conditions permitting the production of the enzyme, and recovering the enzyme from the culture.

16. An isolated enzyme exhibiting β-1,3-glucanase activity, wherein the enzyme is encoded by the DNA construct of claim 1.

17. The enzyme of claim 16, wherein the enzyme has an apparent molecular weight of about 26 KDa.

18. The enzyme of claim 16, wherein the enzyme has a pI in the range of about 3.5 to 4.

* * * * *

UNITED STATES PATENT AND TRADEMARK OFFICE
CERTIFICATE OF CORRECTION

PATENT NO. : 5,919,688

DATED : July 6, 1999

INVENTOR(S) : Ferrer et al.

It is certified that error appears in the above-identified patent and that said Letters Patent is hereby corrected as shown below:

On the title page: Item [54] and Column 1, line 4, delete "Enzyme With B-1, 3-Glucanase"
and insert --Enzyme With β-1, 3-Glucanase--

Col. 29, line 9, claim 14 delete "or"

Signed and Sealed this

Seventh Day of November, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1459 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (B) STRAIN: Oerskovia xanthineolytica LLG109

(ix) FEATURE:
      (A) NAME/KEY: RBS
      (B) LOCATION:344..348

(ix) FEATURE:
      (A) NAME/KEY: CDS
      (B) LOCATION:353..1270

(xi) SEQUENCE DESCRIPTION: SEQ ID NO:1:

```
GGATCCGGTG ATGCGCGAAA CCTTCGTCAT GAGGGTTCGG TGCGCTTGAG ACGCCCCCGC      60

GCTGTCCTAC CGCTGGTGAG GACGGCGCAC ACCGTCCGGT GCATCATTCG GGACGTCGGG     120

CCCAGGAGGT GGTCGGCATC AAATCACGGC ATCGTTCGGA TGACACTCTT CACCGTTGAG     180

CCGGGGCAAC AACCTGTGGT CCTCGTTCGG AGGAGCTCGT CGCAGCCCTC GTGTCAGAGG     240

TGCCCGCTTC GACGCCGGCC CAGGAGATAC GGGTCGCGCA GACCCTCACC ACGTGCGACA     300
```

```
CCGCGGACCC ACACCGACGA TGAAGGCTCT GCCGGCAGAT CTCGGAGAGA TG ATG          355
                                                         Met
                                                          1

AGC CTC CCG CAT GAG CCG TCC TCG CCT TCA AGG CGA ACC CTC ACG TTG       403
Ser Leu Pro His Glu Pro Ser Ser Pro Ser Arg Arg Thr Leu Thr Leu
          5               10              15

ATC CTG GCC GCT GCT GCT GGT CTC GCA CTG GTG GCC GCC TGG ATC GTC       451
Ile Leu Ala Ala Ala Ala Gly Leu Ala Leu Val Ala Ala Trp Ile Val
         20              25              30

ATC GCC ACC AGG TCG TCG CCA CCG ACG AGT CCT CCC ACC ACA GAA GGC       499
Ile Ala Thr Arg Ser Ser Pro Pro Thr Ser Pro Pro Thr Thr Glu Gly
         35              40              45

GGC CAG GTC ACG ACC CCA GCC CCC AAC GAC CCC ACC GCC GTC ACC CCC       547
Gly Gln Val Thr Thr Pro Ala Pro Asn Asp Pro Thr Ala Val Thr Pro
50              55              60              65

GAG AGC CTC GCC TGG TCC GAC GAG TTC GAC GGC GCC GCG GGG TCG GCG       595
Glu Ser Leu Ala Trp Ser Asp Glu Phe Asp Gly Ala Ala Gly Ser Ala
             70              75              80

CCG AAC CCC GAC GTG TGG AAC CAC GAG ACC GGC GCC GGC GGT TGG GGC       643
Pro Asn Pro Asp Val Trp Asn His Glu Thr Gly Ala Gly Gly Trp Gly
         85              90              95

AAC GCC GAG CTC CAG AAC TAC ACG ACG TCG CGG GTG AAC TCG GCG CTC       691
Asn Ala Glu Leu Gln Asn Tyr Thr Thr Ser Arg Val Asn Ser Ala Leu
         100             105             110

GAC GGT CAG GGC AAC CTG GTC ATC ACC GCG CTC CAG GAG AGC GAC GGG       739
Asp Gly Gln Gly Asn Leu Val Ile Thr Ala Leu Gln Glu Ser Asp Gly
         115             120             125

TCG TAC ACG TCC GCA CGC TTG ACC ACG CAG GGC AAC GTC CAG CCG CAG       787
Ser Tyr Thr Ser Ala Arg Leu Thr Thr Gln Gly Asn Val Gln Pro Gln
130             135             140             145

TTC GGT CGA ATA GAG GCG CGC ATC CAG ATC CCG CGT GGC CAG GGC ATC       835
Phe Gly Arg Ile Glu Ala Arg Ile Gln Ile Pro Arg Gly Gln Gly Ile
              150             155             160

TGG TCC GCG TTC TGG ATG GTC GGA GCG AAC CTG CCC GAC ACC CCC TGG       883
Trp Ser Ala Phe Trp Met Val Gly Ala Asn Leu Pro Asp Thr Pro Trp
          165             170             175

CCT ACC TCC GGT GAG ATC GAC ATC ATG GAG AAC GTG GGC AAT GCG CCC       931
Pro Thr Ser Gly Glu Ile Asp Ile Met Glu Asn Val Gly Asn Ala Pro
          180             185             190

CAC GAG GTC CAC GGC ACG GTC CAC GGG CCT GGG TAC TCC GGG GAC AAC       979
His Glu Val His Gly Thr Val His Gly Pro Gly Tyr Ser Gly Asp Asn
         195             200             205

GGC ATC ATG GGC ACC TAC CAG CAT CCG CAA GGG TGG TCG TTC GCC GAC      1027
Gly Ile Met Gly Thr Tyr Gln His Pro Gln Gly Trp Ser Phe Ala Asp
210             215             220             225

GAC TTC CAC ACC TTC GGC ATC GAT TGG ACG CCG GGT GAG ATC ACG TGG      1075
Asp Phe His Thr Phe Gly Ile Asp Trp Thr Pro Gly Glu Ile Thr Trp
             230             235             240

CTC GTT GAC GGG CAG GAG TAT CAC CGC GTG ACG ACC GCG GAT GTC GGT      1123
Leu Val Asp Gly Gln Glu Tyr His Arg Val Thr Thr Ala Asp Val Gly
         245             250             255

GCC AAC CAG TGG GTG TTC GAC CAG CCG TTC TTC CTC ATC CTC AAC GTC      1171
Ala Asn Gln Trp Val Phe Asp Gln Pro Phe Phe Leu Ile Leu Asn Val
         260             265             270

GCC ATC GGC GGC CAG TGG CCC GGC AAC CCC GAC GCA ACG ACC CCG TTT      1219
Ala Ile Gly Gly Gln Trp Pro Gly Asn Pro Asp Ala Thr Thr Pro Phe
         275             280             285

CCG CAG CAG ATG AAG GTC GAC TAC GTG CGG GTC TAC GAC AAC GCG ACG      1267
Pro Gln Gln Met Lys Val Asp Tyr Val Arg Val Tyr Asp Asn Ala Thr
290             295             300             305
```

```
CAG TAGCCACCCT CGCGCGGGCG CCGCCGGTTC GATCGGGAAC GGGTCGAGAC        1320
Gln

GCTGGTGGGT GAACGACCAG CGTCGACCTG GGGCAACCTG ACCGTTGCTG GTGCAGCTCG  1380

GTCATCCTGT GACTCCGGGG TCTACGGCGG ATGCGCATCG TCGCTGCCGC CCGGACGGGC  1440

GGTAGGGGCG TCAGGTACC                                              1459
```

(2) INFORMATION FOR SEQ ID NO:2:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Leu Pro His Glu Pro Ser Ser Pro Ser Arg Arg Thr Leu Thr
 1               5                  10                  15

Leu Ile Leu Ala Ala Ala Ala Gly Leu Ala Leu Val Ala Ala Trp Ile
            20                  25                  30

Val Ile Ala Thr Arg Ser Ser Pro Thr Ser Pro Pro Thr Thr Glu
        35                  40                  45

Gly Gly Gln Val Thr Thr Pro Ala Pro Asn Asp Pro Thr Ala Val Thr
 50                  55                  60

Pro Glu Ser Leu Ala Trp Ser Asp Glu Phe Asp Gly Ala Ala Gly Ser
 65                  70                  75                  80

Ala Pro Asn Pro Asp Val Trp Asn His Glu Thr Gly Ala Gly Gly Trp
                85                  90                  95

Gly Asn Ala Glu Leu Gln Asn Tyr Thr Thr Ser Arg Val Asn Ser Ala
            100                 105                 110

Leu Asp Gly Gln Gly Asn Leu Val Ile Thr Ala Leu Gln Glu Ser Asp
        115                 120                 125

Gly Ser Tyr Thr Ser Ala Arg Leu Thr Thr Gln Gly Asn Val Gln Pro
130                 135                 140

Gln Phe Gly Arg Ile Glu Ala Arg Ile Gln Ile Pro Arg Gly Gln Gly
145                 150                 155                 160

Ile Trp Ser Ala Phe Trp Met Val Gly Ala Asn Leu Pro Asp Thr Pro
                165                 170                 175

Trp Pro Thr Ser Gly Glu Ile Asp Ile Met Glu Asn Val Gly Asn Ala
            180                 185                 190

Pro His Glu Val His Gly Thr Val His Gly Pro Gly Tyr Ser Gly Asp
        195                 200                 205

Asn Gly Ile Met Gly Thr Tyr Gln His Pro Gln Gly Trp Ser Phe Ala
210                 215                 220

Asp Asp Phe His Thr Phe Gly Ile Asp Trp Thr Pro Gly Glu Ile Thr
225                 230                 235                 240

Trp Leu Val Asp Gly Gln Glu Tyr His Arg Val Thr Thr Ala Asp Val
                245                 250                 255

Gly Ala Asn Gln Trp Val Phe Asp Gln Pro Phe Phe Leu Ile Leu Asn
            260                 265                 270

Val Ala Ile Gly Gly Gln Trp Pro Gly Asn Pro Asp Ala Thr Thr Pro
        275                 280                 285

Phe Pro Gln Gln Met Lys Val Asp Tyr Val Arg Val Tyr Asp Asn Ala
290                 295                 300

Thr Gln
305
```

(2) INFORMATION FOR SEQ ID NO: 3:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Oerskovia xanthineolytica LLG109

(xi) SEQUENCE DESCRIPTION:SEQ ID NO:3:

```
TTTGTGGATG GGCAGCAGTT CCACCGCGTC ACGCGCCGCG AGCTCGGCGC GAACGCCTGG        60

GTGTTCGACC AGCCGTTCTT CCTCATCCTC AACGTCGCGG TCGGCGGGCA GTGGCCGGGC       120

TACCCCGACG GCACGACCCA GCTCCCGCAG CAGATGAAGG TCGATTACGT CCGCGTCTAC       180

G                                                                      181
```

(2) INFORMATION FOR SEQ ID NO:4:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:4:

```
Phe Val Asp Gly Gln Gln Phe His Arg Val Thr Arg Arg Glu Leu Gly
            5                  10                  15

Ala Asn Ala Trp Val Phe Asp Gln Pro Phe Phe Leu Ile Leu Asn Val
             20                  25                  30

Ala Val Gly Gly Gln Trp Pro Gly Tyr Pro Asp Gly Thr Thr Gln Leu
         35                  40                  45

Pro Gln Gln Met Lys Val Asp Tyr Val Arg Val Tyr
     50                  55                  60
```